United States Patent [19]

Chapman et al.

[11] Patent Number: 5,430,128
[45] Date of Patent: Jul. 4, 1995

[54] PEPTIDYL DERIVATIVES AS INHIBITORS OF INTERLEUKIN-1β CONVERTING ENZYME

[75] Inventors: Kevin T. Chapman, Scotch Plains; Malcolm MacCoss, Freehold; Adnan Mjalli, Rahway, all of N.J.

[73] Assignee: Merck & Co., Inc., Rahway, N.J.

[21] Appl. No.: 342,991

[22] Filed: Nov. 21, 1994

Related U.S. Application Data

[63] Continuation of Ser. No. 67,412, May 25, 1993, abandoned, which is a continuation of Ser. No. 839,590, Feb. 21, 1992, abandoned.

[51] Int. Cl.$^6$ .................. A61K 38/00; C07K 5/00; C07K 7/00; C07K 17/00
[52] U.S. Cl. .................. 530/330; 530/331; 562/571
[58] Field of Search .............. 530/330, 331; 562/571

[56] References Cited

U.S. PATENT DOCUMENTS 5,055,451 10/1991 Krantz et al. .................. 514/19

FOREIGN PATENT DOCUMENTS

0618223A2 10/1994 European Pat. Off. .
9115577 10/1991 WIPO .
WO93/09135 5/1993 WIPO .

OTHER PUBLICATIONS

The Merck Veterinary Manual Seventh Edition (1991), pp. 1019–1025 "Diseases of Rats and Mice".
Sleath et al. J. Biol. Chem: vol. 265 14526–14528 (1990).
Howard et al., J. Immun. vol. 147, 2964–2969 (Nov. 1991).
Black, et al. J. Biol. Chem. 263, 9437–9442 (1988).
Black, et al. J. Biol. Chem. 264, 5323–5326 (1989).
Black et al. FEB LETT. 247, 286–290 (1989).
Kostura, et al. Proc. Natl. Acad. Sci. 86, 5227–5231 (1989).

*Primary Examiner*—Jill Warden
*Assistant Examiner*—Sheela J. Huff
*Attorney, Agent, or Firm*—Curtis C. Panzer; David L. Rose

[57] ABSTRACT

Novel peptidyl derivatives of formula I are found to be potent inhibitors of interleukin-1β converting enzyme (ICE). Compounds of formula I may be useful in the treatment of inflammatory or immune-based diseases of the lung and airways; central nervous system and surrounding membranes; the eyes and ears; joints, bones, and connective tissues; cardiovascular system including the pericardium; the gastrointestinal and urogenital systems; the skin and mucosal membranes. Compounds of formula I are also useful in treating the complications of infection (e.g., gram negative shock) and tumors in which IL 1 functions as an autocrine growth factor or as a mediator of cachexia.

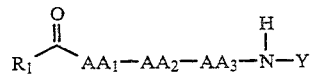

17 Claims, No Drawings

PEPTIDYL DERIVATIVES AS INHIBITORS OF INTERLEUKIN-1β CONVERTING ENZYME

This is a continuation of application Ser. No. 08/067,412, filed May 25, 1993, now abandoned, which is a continuation of application Ser. No. 07/839,590, filed Feb. 21, 1992, now abandoned.

BACKGROUND OF THE INVENTION

This invention relates to substituted peptidyl derivatives useful in the treatment of inflammation in lung, central nervous system, kidney, joints, endocardium, pericardium, eyes, ears, skin, gastrointestinal tract and urogenital system. More particularly, this invention relates substituted peptidyl lactones and open forms thereof that are useful inhibitors of interleukin-1β converting enzyme (ICE). Interleukin-1β converting enzyme (ICE) has been identified as the enzyme responsible for converting precursor interleukin-1β (IL-1β) to biologically active IL-1β.

Mammalian interleukin-1 (IL-1) is an immunoregulatory protein secreted by cell types as part of the inflammatory response. The primary cell type responsible for IL-1 production is the peripheral blood monocyte. Other cell types have also been described as releasing or containing IL-1 or IL-1 like molecules. These include epithelial cells (Luger, et al., J. Immunol. 127:1493-1498 (1981), Leet al., J. Immunol. 138:2520-2526 (1987) and Lovett and Larsen, J. Clin. Invest. 82:115-122 (1988), connective tissue cells (Ollivierre et al., Biochem. Biophys. Res. Comm. 141:904-911 (1986), Le et al, J. Immunol. 138:2520-2526 (1987), cells of neuronal origin (Giulian et al., J. Esp. Med. 164: 594–604 (1986) and leukocytes (Pistoia et al., J. Immunol. 136:1688-1692 (1986), Acres et al., Mol. Immuno. 24:479–485 (1987), Acres et al., J. Immunol. 138:2132-2136 (1987) and Lindenmann et al., J. Immunol 140:837-839 (1988).

Biologically active IL-1 exists in two distinct forms, IL-1α with an isoelectric point of about pI 5.2 and IL-1β with an isoelectric point of about 7.0 with both forms having a molecular mass of about 17,500 (Bayne et al., J. Esp. Med. 163: 1267-1280 (1986) and Schmidt, J. Esp. Med. 160:772 (1984). The polypeptides appear evolutionarily conserved, showing about 27-33% homology at the amino acid level (Clark et al., Nucleic Acids Res. 14: 7897-7914 (1986).

Mammalian IL-1β is synthesized as a cell associated precursor polypeptide with a molecular mass of about 31.4 kDa (Limjuco et al., Proc. Natl. Acad. Sci USA 83:3972-3976 (1986). Precursor IL-1β is unable to bind to IL-1 receptors and is biologically inactive (Mosley et al., J. Biol. Chem. 262:2941-2944 (1987). Biological activity appears dependent upon some form of proteolytic processing which results in the conversion of the precursor 31.5 kDa form to the mature 17.5 kDa form. Evidence is growing that by inhibiting the conversion of precursor IL-1β to mature IL-1β, one can effectively inhibit the activity of interleukin-1.

Mammalian cells capable of producing IL-1β include, but are not limited to, karatinocytes, endothelial cells, mesangial cells, thymic epithelial cells, dermal fibroblasts, chondrocytes, astrocytes, glioma cells, mononuclear phagocytes, granulocytes, T and B lymphocytes and NK cells.

As discussed by J. J. Oppenheim, et al. Immunology Today, vol. 7(2):45-56 (1986), the activities of interleukin-1 are many. It has been observed that catabolin, a factor that promotes degradation of cartilage matrix, also exhibited the thymocyte comitogenic activities of IL-1 and stimulates chondrocytes to release collagenase neutral proteases and plasminogen activator. In addition, a plasma factor termed proteolysis inducing factor stimulates muscle cells to produce prostaglandins which in turn leads to proteolysis, the release of amino acids and, in the long run, muscle wasting, and appears to represent a fragment of IL-1 with fever-inducing, acute phase response and thymocyte co-mitogenic activities.

IL-1 has multiple effects on cells involved in inflammation and wound healing. Subcutaneous injection of IL-1 leads to margination of neutrophils and maximal extravascular infiltration of the polymorphonuclear leukocytes (PMN). In vitro studies reveal IL-1 to be a chemotactic attractant for PMN to activate PMN to metabolize glucose more rapidly to reduce nitroblue tetrazolium and to release their lysozomal enzymes. Endothelial cells are stimulated to proliferate by IL-1 to produce thromboxane, to become more adhesive and to release procoagulant activity. IL-1 also enhances collagen type IV production by epidermal cells, induces osteoblast proliferation and alkaline phosphatase production and stimulates osteoclasts to resorb bone. Even macrophages have been reported to be chemotactically attracted to IL-1 to produce prostaglandins in response to IL-1 and to exhibit a more prolonged and active tumoricidal state.

IL-1 is also a potent bone resorptive agent capable upon infusion into mice of causing hypercaleemia and inctuas in bone resorptive surface as revealed by his to morphometry Sabatini, M. et al., PNAS 85: 5235-5239, 1988.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix. Such diseases include periodonate diseases interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

SUMMARY OF THE INVENTION

Novel peptidyl derivatives of formula I are found to be potent inhibitors of interleukin-1β converting enzyme (ICE). Compounds of formula I are useful in the treatment of deseases including inflammation in lung, central nervous system, kidney, joints, endocardium, pericardium, eyes, ears, skin, gastrointestinal tract and urogenital system.

DETAILED DESCRIPTION OF THE INVENTION

The invention encompasses compounds of formula I.

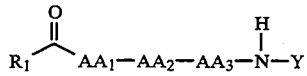

or a pharmaceutically acceptable salt thereof: wherein Y is:

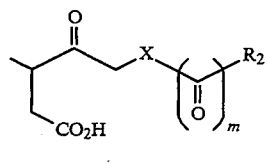

X is S or O;
m is 0 or 1;
$R_1$ is
  (a) substituted $C_{1-6}$ alkyl, wherein the substituent is selected from
    (1) hydrogen,
    (2) hydroxy,
    (3) halo,
    (4) $C_{1-3}$ alkyloxy,
    (5) $C_{1-3}$ alkylthio,
    (6) phenyl $C_{1-3}$ alkyloxy, and
    (7) phenyl $C_{1-3}$ alkylthio;
  (b) aryl $C_{1-6}$ alkyl wherein the aryl group is selected from the group consisting of:
    (1) phenyl,
    (2) naphthyl,
    (3) pyridyl,
    (4) furyl,
    (5) thienyl,
    (6) thiazolyl,
    (7) isothiazolyl,
    (8) imidazolyl,
    (9) benzimidazolyl,
    (10) pyrazinyl,
    (11) pyrimidyl,
    (12) quinolyl,
    (13) isoquinolyl,
    (14) benzofuryl,
    (15) benzothienyl,
    (16) pyrazolyl,
    (17) indolyl,
    (18) purinyl,
    (19) isoxazolyl, and
    (20) oxazolyl,
  and mono and di-substituted aryl as defined above in items (1) to (20) wherein the substitutents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;
$R_2$ is
  (a) tetra or penta substituted phenyl wherein the substitutents are individually selected from the group consisting of
    (1) $C_{1-3}$alkoxy,
    (2) halo,
    (3) hydroxy,
    (4) cyano,
    (5) carboxy,
    (6) $C_{1-3}$alkyl,
    (7) trifruoromethyl,
    (8) trimethylamino,
    (9) benzyloxy,
  (b) mono, di or tri substituted aryl wherein the aryl is selected from the group consisting of phenyl, 1-napthyl, 9-anthracyl and 2, 3, or 4 pyridyl, and the substituents are individually selected from the group consisting of
    (1) phenyl,
    (2) halo,
    (3) $C_{1-3}$alkyl,
    (4) perfluoro $C_{1-3}$alkyl,
    (5) nitro,
    (6) cyano,
    (7) $C_{1-3}$alkylcarbonyl,
    (8) phenylcarbonyl,
    (9) carboxy,
    (10) aminocarbonyl,
    (11) mono and di $C_{1-3}$alkylaminocarbonyl,
    (12) formyl,
    (13) $SO_3H$,
    (14) $C_{1-3}$alkyl sulfonyl,
    (15) phenyl sulfonyl,
    (16) formamido,
    (17) $C_{1-3}$alkylcarbonylamino,
    (18) phenylcarbonylamino,
    (19) $C_{1-3}$alkoxycarbonyl,
    (20) $C_{1-3}$alkylsulfonamido carbonyl,
    (21) phenylsulfonamido carbonyl,
    (22) $C_{1-3}$alkyl carbonylamino sulfonyl,
    (23) phenylcarbonylamino sulfonyl,
    (24) $C_{1-3}$alkyl amino,
    (25) mono di and tri $C_{1-3}$alkyl amino,
    (26) amino,
    (26) hydroxy, and
    (27) $C_{1-3}$alkyloxy;
$AA_1$ is independently selected from the group consisting of
  (a) a single bond, and
  (b) an amino acid of formula AI

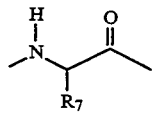

wherein $R_7$ is selected from the group consisting of:
  (a) hydrogen,
  (b) substituted $C_{1-6}$ alkyl, wherein the substituent is selected from
    (1) hydrogen,
    (2) hydroxy,
    (3) halo,
    (4) —S—$C_{1-4}$ alkyl
    (5) —SH
    (6) $C_{1-6}$ alkylcarbonyl,
    (7) carboxy,

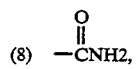

(9) amino carbonyl amino,

(10) C$_{1-4}$ alkylamino, wherein the alkyl moiety is substituted with hydrogen or hydroxy, and the amino is substituted with hydrogen or CBZ,
(11) guanidino, and
(c) aryl C$_{1-6}$ alkyl, wherein aryl is defined as immediately above, and wherein the aryl may be mono and di-substituted, the substituents being each independently C$_{1-6}$alkyl, halo, hydroxy, C$_{1-6}$alkyl amino, C$_{1-6}$alkoxy, C$_{1-6}$alkylthio, and C$_{1-6}$alkylcarbonyl;

AA$_2$ is an amino acid of formula AII

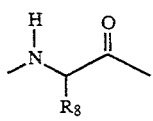

AA$_3$ is an amino acid of formula AIII

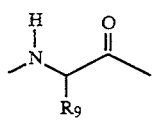

wherein R$_8$ and R$_9$ are each independently selected from the group consisting of
(a) hydrogen,
(b) substituted C$_{1-6}$ alkyl, wherein the substituent is selected from
(1) hydrogen,
(2) hydroxy,
(3) halo,
(4) —S—C$_{1-4}$ alkyl
(5) —SH
(6) C$_{1-6}$ alkylcarbonyl,
(7) carboxy,

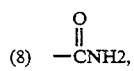

(9) amino carbonyl amino,
(10) C$_{1-4}$ alkylamino, wherein the alkyl moiety is substituted with hydrogen or hydroxy, and the amino is substituted with hydrogen or CBZ,
(11) guanidino, and
(c) aryl C$_{1-6}$ alkyl, wherein aryl is defined as immediately above, and wherein the aryl may be mono and di-substituted, the substituents being each independently C$_{1-6}$alkyl, halo, hydroxy, C$_{1-6}$alkyl amino, C$_{1-6}$alkoxy, C$_{1-6}$alkylthio, and C$_{1-6}$alkylcarbonyl.

One class of this genus is the compounds wherein:
R$_1$ is
(a) substituted C$_{1-6}$ alkyl, wherein the substituent is selected from
(1) hydrogen,
(2) hydroxy,
(3) chloro or fluoro,
(4) C$_{1-3}$ alkyloxy, and
(5) phenyl C$_{1-3}$ alkyloxy,
(b) aryl C$_{1-6}$ alkyl wherein the aryl group is selected from the group consisting of
(1) phenyl,
(2) naphthyl,
(3) pyridyl,
(4) furyl,
(5) thienyl,
(6) thiazolyl,
(7) isothiazolyl,
(8) benzofuryl,
(9) benzothienyl,
(10) indolyl,
(11) isooxazolyl, and
(12) oxazolyl, and mono and di-substituted C$_{6-10}$aryl as defined above in items (1) to (12) wherein the substitutents are independently C$_{1-4}$alkyl, halo, and hydroxy;

AA$_1$ is independently selected from the group consisting of
(a) a single bond, and
(b) an amino acid of formula AI

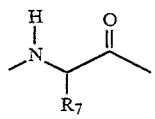

wherein R$_7$ is selected from the group consisting of
(a) hydrogen,
(b) substituted C$_{1-6}$ alkyl, wherein the substituent is selected from
(1) hydrogen,
(2) hydroxy,
(3) halo,
(4) —S—C$_{1-4}$ alkyl
(5) —SH
(6) C$_{1-6}$ alkylcarbonyl,
(7) carboxy,

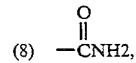

(9) C$_{1-4}$ alkylamino, and C$_{1-4}$ alkylamino wherein the alkyl moiety is substituted with an hydroxy, and
(10) guanidino,
(11) C$_{1-4}$ alkyloxy,
(12) phenylC$_{1-4}$alkyloxy,
(13) phenylC$_{1-4}$ alkylthio, and
(c) aryl C$_{1-6}$ alkyl, wherein the aryl group is elected from the group consisting of
(1) phenyl,
(2) naphthyl,
(3) pyridyl,
(4) furyl,
(5) thienyl,
(6) thiazolyl,
(7) isothiazolyl,
(8) benzofuryl,
(9) benzothienyl,
(10) indolyl,
(11) isooxazolyl, and
(12) oxazolyl, and wherein the aryl may be mono and di-substituted, the substituents being each independently C$_{1-6}$alkyl, halo, hydroxy, C$_{1-6}$alkyl amino, C$_{1-6}$alkoxy, C$_{1-6}$alkylthio, and C$_{1-6}$alkylcarbonyl;

AA$_2$ is an amino acid of formula AII

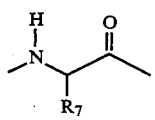

AA3 is an amino acid of formula AIII

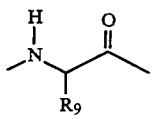

wherein R8 and R9 are each independently selected from the group consisting of
(a) hydrogen,
(b) $C_{1-6}$ alkyl, wherein the substituent is selected from
  (1) hydrogen,
  (2) hydroxy,
  (3) halo,
  (4) —S—$C_{1-4}$ alkyl
  (5) —SH
  (6) $C_{1-6}$ alkylcarbonyl,
  (7) carboxy,

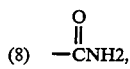

(9) $C_{1-4}$ alkylamino, and $C_{1-4}$ alkyl amino wherein the alkyl moeity is substituted with an hydroxy, and
  (10) guanidino, and
(c) aryl $C_{1-6}$ alkyl, wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

Within this class are the compounds wherein AA1, AA2 and AA3, are each independently selected from the group consisting of the L- and D- forms of the amino acids including glycine, alanine, valine, leucine, isoleucine, serine, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline.

Alternatively, within this class are the subclass of compounds wherein
R1 is $C_{1-3}$alkyl;
R8 and R9 are each individually
  (a) hydrogen,
  (b) $C_{1-6}$alkyl,
  (c) mercapto $C_{1-6}$alkyl,
  (d) hydroxy $C_{1-6}$alkyl,
  (e) carboxy $C_{1-6}$alkyl,
  (g) aminocarbonyl $C_{1-6}$alkyl,
  (h) mono- or di-$C_{1-6}$alkyl amino $C_{1-6}$alkyl,
  (i) guanidino $C_{1-6}$alkyl,
  (j) amino-$C_{1-6}$alkyl or N-substituted amino-$C_{1-6}$alkyl wherein the substituent is carbobenzoxy,
  (k) carbamyl $C_{1-6}$alkyl, or
  (l) aryl $C_{1-6}$alkyl, wherein the aryl group is selected from phenyl and indolyl, and the aryl group may be substituted with hydroxy, $C_{1-3}$ alkyl.

Exemplifying the invention are the following compounds:
(a) N-(N-phenylpropionyl-valinyl-alaninyl)-3-amino-4-oxo-5-(2,6-bistrifluoromethylbenzoyloxy) pentanoic acid;
(b) N-(N-phenylpropionyl-valinyl-alaninyl)-3-amino-4-oxo-5-benzoyloxy pentanoic acid; and
(c) N-(N-Acetyl-tyrosinyl-valinyl-alaninyl)-3-amino-4-oxo-5-(pentafluorobenzoyloxy) pentanoic acid.

This invention also concerns to pharmaceutical composition and methods of treatment of interleukin-1 and interleukin-1β mediated or implicated disorders or diseases (as described above) in a patient (including man and/or mammalian animals raised in the dairy, meat, or fur industries or as pets) in need of such treatment comprising administration of interleukin-1β inhibitors of formula (I) as the active constituents.

Illustrative of these aspects, this invention concerns pharmaceutical compositions and methods of treatment of diseases selected from septic shock, allograft rejection, inflammatory bowel disease and rheumatoid arthritis in a patient in need of such treatment comprising:
administration of an interleukin-1β inhibitor of formula (I) as the active constituent.

Compounds of the instant invention are conveniently prepared using the procedures described generally below and more explicitly described in the Example section thereafter.

Scheme

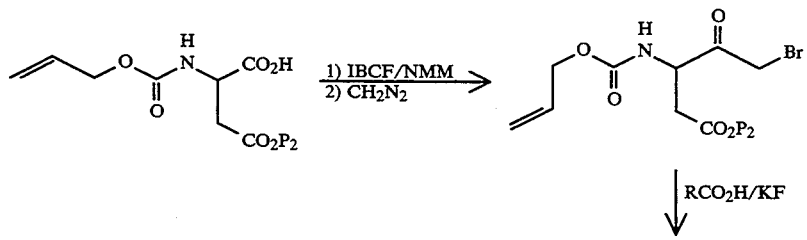

-continued

Scheme

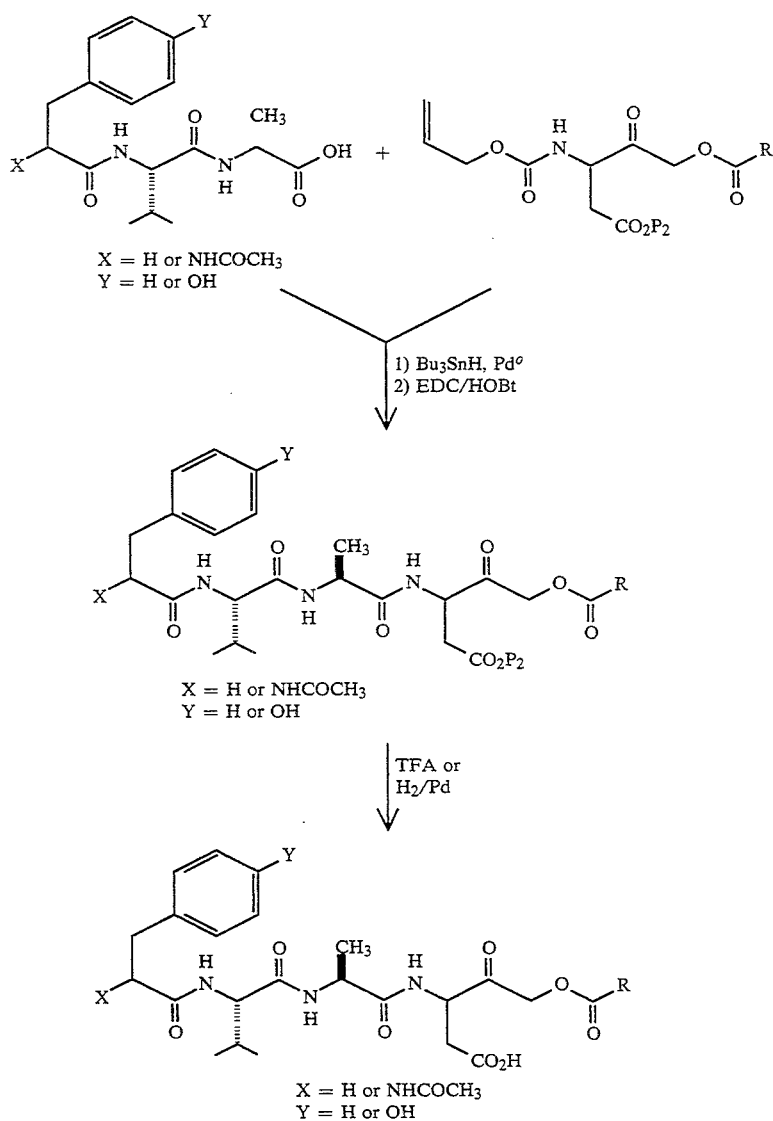

X = H or NHCOCH3
Y = H or OH

The described compounds can be prepared as follows. An alloc protected aspartic acid β-ester can be converted to the corresponding diazomethylketone using isobutylchloroformate and N-methylmorpholine followed by excess diazomethane. The bromomethylketone can then be formed by treatment of the diazomethylketone with hydrobromic acid in ether. Bromomethylketones react with carboxylic acids in the presence of potassium fluoride in dimethylformamide to afford the corresponding presence of potassium fluoride in dimethylformamide to afford the corresponding acyloxymethylketone. The alloc group can then be removed, and the product coupled to a di, or tripepride using first tributyl tin hydride and bistriphenylphosphine palladium dichloride, and then ethyl dimethylaminopropyl carbodimide and hydroxybenzotriazole. The carboxyllic acid protecting group is then removed to afford the desired products.

The compounds of the instant invention of the formula (I), as represented in the Examples hereinunder shown to exhibit in vitro inhibitory activities with respect to interleukin-1β. In particular, these compounds have been shown to inhibit interleukin-1β converting enzyme from cleaving precusor interleukin-1β as to form active interleukin-1β at a Ki of less than 1 uM.

This invention also relates to a method of treatment for patients (including man and/or mammalian animals raised in the dairy, meat, or fur industries or as pets) suffering from disorders or diseases which can be attributed to IL-1/ICE as previously described, and more specifically, a method of treatment involving the administration of the IL-1/ICE inhibitors of formula (I) as the active constituents.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis.

Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix such as interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

For the treatment the above mentioned diseases, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

Additional methods of making compounds of this invention are known in the art such as U.S. Pat. No. 5,055,451, issued to Krantz et. al., Oct. 8, 1991 which is hereby incorporated by reference.

EXAMPLE 1

N-(N-Phenylpropionyl-valinyl-alaninyl)-3-amino-5-benzoyloxy-4-oxopentanoic acid:

STEP A

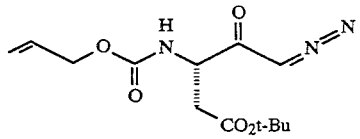

N-Allyloxycarbonyl-3-amino-5-diazo-4-oxopentanoic acid β-t-butyl ester

To a solution of Alloc-aspartic acid β-t-butyl ester (6.23 g, 22.8 mmol) and 4-methyl morpholine (2.63 mL, 23.94 mmol) in 50 mL of freshly distilled dichloromethane at $-10°$ C. was added freshly distilled isobutyl chloroformate (3.04 mL, 23.48 mmol). After 15 min, the solution was filtered and excess ethereal diazomethane was added. The mixture was stirred at 0° C. for 1 h and concentrated. The mixture was purified by MPLC on silica-gel ($35 \times 350$ mm column, eluting with 25% ethyl acetate in hexane) to give the title compound as a pale yellow oil: $^1$H NMR (400 MHz, CDCl$_3$) δ5.91 (m, 1H), 5.62 (br s, 1H), 5.31 (d, 1H), 5.24 (d, 1H), 4.61 (br d, 2H), 4.50 (m, 1H), 2.92 (dd, 1H), 2.60 (dd, 1H), 1.43 (s, 9H).

STEP B

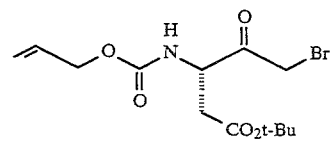

N-Allyloxycarbonyl-3-amino-5-bromo-4-oxopentanoic acid β-t-butyl ester

To a solution of N-Allycarbonyl-3-amino-5-diazo-4-oxopentanoic acid β-t-butyl ester in ether was added approximately one equivalent of 30% HBr in acetic acid. After 30 min, the solution was diluted with ether and washed three times with water. The combined organic layers were dried over magnesium sulphate, filtered, and concentrated. The product was purified by MPLC on silica-gel eluting with 20% ethyl acetate in hexane to afford the title compound as a colorless solid: $^1$H NMR (400 MHz, CD$_3$OD) δ5.93 (m, 1H), 5.31 (d, 1H), 5.19 (d, 1H), 4.69 (t, 1H), 4.58 (br d, 2H), 4.29 (AB, 2H), 2.82 (dd, 1H), 2.63 (dd, 1H), 1.43 (s, 9H).

STEP C

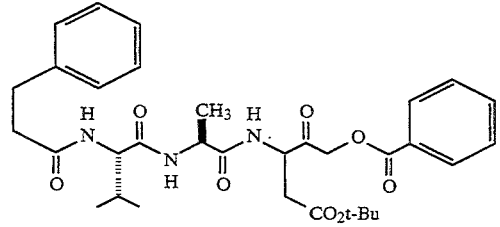

N-(N-Phenylpropionyl-valinyl-alaninyl)-3-amino-5-benzoyloxy-4-oxopentanoic acid B-t-butyl ester To a solution of N-Allyoxycarbonyl-3-amino-5-benzoyloxy-4-oxopentanoic acid β-t-butyl ester (266 mg, 0.679 mmol) and Phenylpropionyl-valinyl-alanine (228 mg, 0.679 mmol) in 5 mL each of dichloromethane and DMF was added ~20 mg of Pd(PPh$_3$)$_2$Cl$_2$ followed by dropwise addition of tributyltin hydride (274 μL, 1.02 mmol). After 5 min, the mixture was cooled to 0° C. and hydroxybenzotriazole (138 mg, 1.02 mmol) and ethyldimethylaminopropyl carbodiimide (151 mg, 0.815 mmol) were added. After 16 hours, the mixture was diluted with ethyl acetate and washed three times with 1 N hydrochloric acid and three times with saturated sodium bicarbonate. The mixture was dried over sodium sulfate, filtered, and concentrated. The product was purified by MPLC on silica-gel eluting with 1:1 ethylacetate:dichloromethane to afford the title compound: $^1$H NMR (200 MHz, CD$_3$OD) δ8.04 (br d, 2H), 7.72–7.10 (m, 8H), 5.13 (s, 2H), 4.78 (t, 1H), 4.4–4.1 (m, 2H), 3.0–2.5 (m, 6H), 2.01 (m, 1H), 1.45 (s, 9H), 1.38 (d, 3H), 0.90 (d, 3H), 0.85 (d,

STEP D

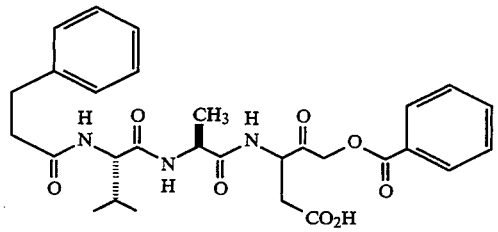

N-(N-Phenylpropionyl-valinyl-alaninyl)-3-amino-5-benzyloxy-4-oxopentanoic acid

N-(N-Phenylpropionyl-valinyl-alanyl)-3-amino-5-benzyloxy-4-oxopentanoic acid β-t-butyl ester was dissolved in trifluoroacetic acid. After 30 min, the mixture was concentrated to afford the title compound: $^1$H NMR (400 MHz, CD$_3$OD ) δ8.04 ( d, 2H), 7.7–7.10 (m, 8H), 5.16 (AB, 2H), 4.78 (t, 1H), 4.33 (q, 1H), 4.12 (d, 1H), 3.0–2.5 (m, 6H), 2.01 (m, 1H), 1.38 (d, 3H), 0.89 (d, 3H), 0.84 (d, 3H).

EXAMPLE 2

N-(N-Phenylpropionyl-valinyl-alaninyl)-3-amino-5-(2,6-bistrifluoromethylbenzoylory)-4-oxopentanoic acid

STEP A

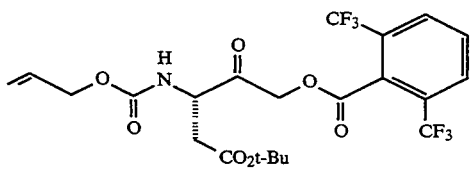

N-Allyoxycarbonyl-3-amino-5-(2,6-bistrifluoromethyl-benzoyloxy)-4-oxopentanoic acid β-t-butyl ester Potassium fluoride (79 mg, 1.35 mmol) and N-Allyoxycarbonyl-3-amino-5-bromo-4-oxopentanoic acid β-t-butyl ester (215 mg, 0.614 mmol) were stirred in 5 mL of DMF for 1 min. 2,6-Bistrifluoromethyl-benzoic acid (158 mg, 0.612 mmol) was added and the mixture stirred for 45 min at ambient temperature. The mixture was diluted with ether, washed three times with water, dried over magnesium sulfate, filtered, and concentrated to afford the title compound: $^1$H NMR (400 MHz, CD$_3$OD) δ8.10 (d, 2H), 7.89 (t, 1H), 5.94 (m, 1H), 5.32 (d, 1H), 5.25–5.1 (m, 3H), 4.63 (m, 1H), 4.59 (m, 2H), 2.83 (dd, 1H), 2.64 (dd, 1H), 1.43 (s, 9H).

STEP B

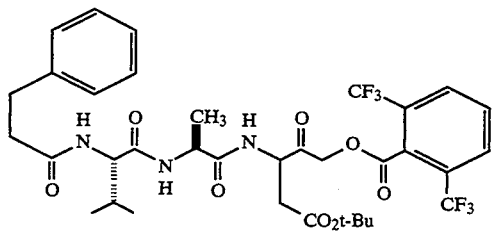

N-(N-Phenylpropionyl-valinyl-alaninyl)-3-amino-5-(2,6-bietrifluoromethylbenzoyloxy)-4-oxopentanoic acid β-t-butyl ester To a solution of N-Allyoxycarbonyl-3-amino-5-(2,6-bistrifluoromethyl- benzoyloxy)-4-oxopentanoic acid β-t-butyl ester (348 mg, 0.630 mmol) and Phenylpropionyl-valinyl-alanine (212 mg, 0.630 mmol) in 5 mL each of dichloromethane and DMF was added ~20 mg of Pd(PPh$_3$)$_2$Cl$_2$ followed by dropwise addition of tributyltin hydride (254 μL, 0.95 mmol). After 5 min, the mixture was cooled to 0° C. and hydroxybenzotriazole (128 mg, 0.945 mmol) and ethyldimethylaminopropyl carbodiimide (145 mg, 0.756 mmol) were added. After 16 hours, the mixture was diluted with ethyl acetate and washed three times with 1 N hydrochloric acid and three times with saturated sodium bicarbonate. The mixture was dried over sodium sulfate, filtered, and concentrated. The product was purified by MPLC on silica-gel eluting with 30% ethylacetate in dichloromethane to afford the title compound: $^1$H NMR (200 MHz, CD$_3$OD) δ8.09 (d, 2H), 7.88 (t, 1H), 7.3–7.1 (m, 5H), 5.16 (AB, 2H), 4.77 (t, 1H), 4.45–4.1 (m, 2H), 3.0–2.5 (m, 6H), 2.01 (m, 1H), 1.43 (S, 9H), 1.38 (2d's, 3H), 0.95–0.80 (4d's, 6H).

STEP C

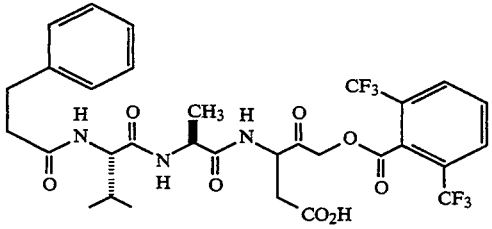

N-(N-Phenylpropionyl-valinyl-alaninyl)-3-amino-5-(2,6-bistrifluoromethylbenzoyloxy)-4-oxopentanoic acid N-(N-Phenylpropionyl-valinyl-alaninyl)-3-amino-5-(2,6-bistrifluoromethylbenzoyloxy)-4-oxopentanoic acid β-t-butyl ester was dissolved in trifluoroacetic acid. After 30 min, the mixture was concentrated and the residue purified by MPLC on silica-gel eluting with a gradient of dichloromethane to 1% formic acid and 4% methanol in dichloromethane to afford the title compound as a colorless solid: $^1$H NMR (400 MHz, CD$_3$OD) δ8.10 (d, 2H), 7.89 (t, 1H), 7.3–7.1 (m, 5H), 5.3–5.0 (v br s, 2H), 4.72 (m, 1H), 4.33 (q, 1H), 4.11 (d, 1H), 2.91 (d, 2H), 2.81 (m, 2H), 2.57 (m, 2H), 1.99 (m, 1H), 1.35 (br s, 3H), 0.89 (d, 3H), 0.84 (d, 3H).

EXAMPLE 3

N-(N-Acetyl-Tyrosinyl-Valinyl-Alaninyl)-3-amino-4-Oxo-5-Pentafluorobenzoyloxy pentanoic acid

STEP A

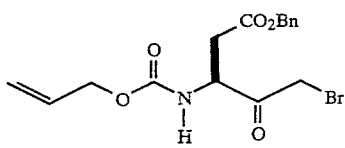

3-Allyloxycarbonylamino-4-oxo-5-Bromopentanoic acid benzyl ester

To a solution of N-alloc-β-benzyl aspartic acid (920 mg, 3.0 mmol) at 0° C. was added NMR (3.6 ml) and IBCF (0.395 mL, 3.6 mmol). The resulting mixture was stirred at 0° C. for 10 min followed by addition of CH$_2$N$_2$/ether and the mixture was stirred for 10 min. 48% HBr(10 mL) was added and the stirring was continued for 20 min. Ether (200 mL) was added and the mixture was washed with water (6×10 mL), Brine (10 mL) and dried over Na$_2$SO$_4$. The solvent was concentrated and the residue was chromatographed over silica (1:3, Ether:Hexane) to provide the Bromomethyl ketone 890 mg. $^1$HNMR (CDCl$_3$), δ7.4–7.22 (5H, m), 5.9 (2H, m), 5.25 (2H, dx3), 4.75 (1H, m), 4.55 (2H, m), 4.15 (2H, s) 2.95 (2H, dx4).

STEP B

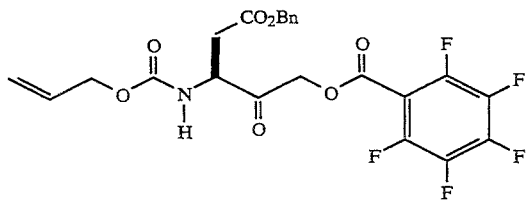

3-Allyloxycarbonylamino-4-oxo-5-Pentafluorobenzoyloxy pentanoic acid benzyl ester To the bromomethyl ketone compound (200 mg, 0.52 mmol) in DMF (5 ml) was added KF (1.144 mmol, 66.56 mg). The resulting mixture was stirred for 3 min. followed by addition of pentafluorobenzoic acid and the mixture was stirred for 1 h. Ether (100 ml) was added, the mixture was washed with aq. NaHCO$_3$ and dried over Na$_2$SO$_4$ the solvent was concentrated and the residue was passed through a block of silica (1:1, ether:hexane) to provide the title compound (175 mg). $^1$HNMR (CDCl$_3$), δ7.35 (5H,m), 5.9 (1H,m) 5.8 (1H,m), 5.25 (2H, dx4), 5.22 (2H, ABq), 5.12 (2H, S) 4.69 (1H,m), 4.58 (1H, d), 3.12 (1H, d), 2.85 (1H,d).

STEP C

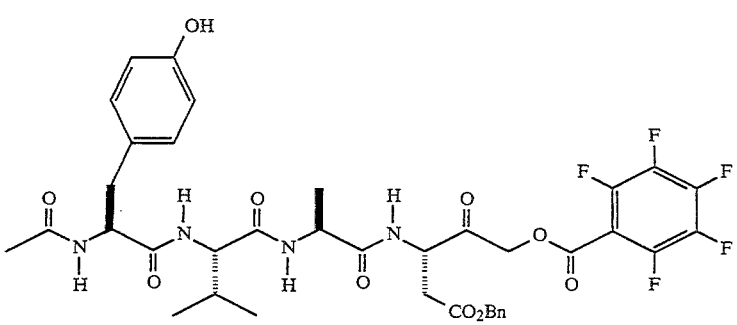

N-(N-Acetyl-Tyrosinyl-Valinyl-Alaninyl)-3-amino-4-oxo-5-Pentafluorobenzoyloxy pentanoic acid benzyl ester To the N-alloc pentafluoro-benzyloxymethyl ketone (130 mg, 0.252 mmol) in CH$_2$Cl$_2$ (3 mL) was added PdCl$_2$(Ph$_3$P)$_2$ (cat.) followed by addition of (Bu)3SnH (0.08mL). The mixture was stirred for 5 min. DMF (10 mL), AcTyr Val Ala (98 mg), HOBT (80 mg) and EDC 45.6 mg) respectively. The resulting mixture was stirred at room temperature over night. EtOAc (100 ml) was added and the mixture washed with aq. NaHCO$_3$ (10 mL). The solvent was concentrated and the residue was chromatographed over silica (95:5/CH2Cl2: MeOH) to provide the title compound (65 mg).

$^1$HNMR (CD$_3$OD) δ7.3 (5H,m), 7.0 (2H, d), 6.67 (2H, m), 5.2 (1H, d), 5.15 (1H,s), 4.85 (2H, ABq), 4.55 (1H,m), 4.25 (1H, d), 4.15 (1H, d), 3.2–2.7 (5H, m), 2.05 (1H, m), 1.9 (3H, d), 1.35 (3H,d), 0.95 (6H, m).

STEP D

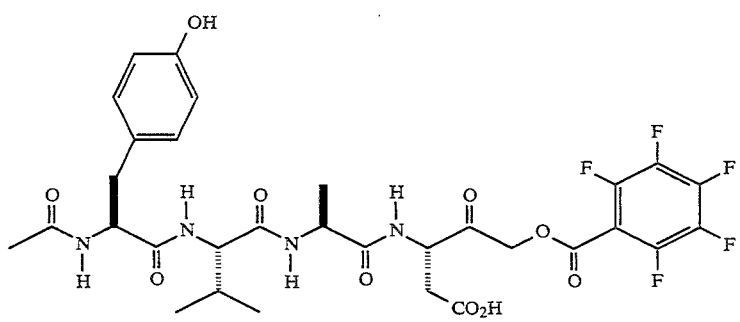

N-(N-Acetyl-Tyrosinyl-Valinyl-Alaninyl)-3-amino-4-Oxo-5-Pentafluorobenzoyloxy pentanoic acid To the benzyl ester (25mg) in MeOH (3 ml) was added 10% Pd/c (cat.) and the mixture was stirred under positive pressure of $H_2$ for 2 h. The mixture was filtered through Celite and the solvent was concentrate to give the title compound (14 mg) which was crystalized from acetone/hexane.

$^1$HNMR ($CD_3OD$) δ7.05 (1H, d), 6.7 (1H, d), 4.9 (2H, ABq), 4.55 (1H, m), 4.3 (1H, m), 3.05-2.7 (4H, m), 2.05 ( 1H, m), 1.92 (3H, s), 1.34 (3H, m), 0.95 (6H, ,5). M/z $M+K^+$ (754.4), $M+Na^+$ (740.3, $M^{+1}$ (718.2), 637.7, 645.6, 563.2, 546.2, 413.2, 376.4, 305.3, 279.2, 205.9, 177.8, 163.1 (base).

What is claimed is:

1. A compound of formula I

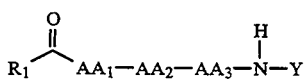

or a pharmaceutically acceptable salt thereof: wherein Y is:

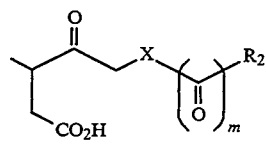

X is O;
m is 0; and
$R_1$ is $C_{1-3}$alkyl or substituted aryl $C_{1-6}$ alkyl wherein aryl is phenyl and the substituent is hydrogen, hydroxy, halo or $C_{1-4}$ alkyl;
$R_2$ is
  (a) tetra or penta substituted phenyl wherein the substitutents are individually selected from the group consisting of
    (1) methoxy,
    (2) halo,
    (3) hydroxy, and
    (4) $C_{1-3}$alkyl,
  (b) di or tri substituted phenyl, wherein the substituents are individually selected from the group consisting of
    (1) halo,
    (2) $C_{1-3}$alkyl,
    (3) trifluoro methyl, and
AA1 is a single bond or an amino acid of formula AI

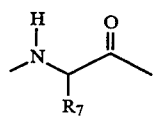

wherein $R_7$ is selected from the group consisting of aryl $C_{1-6}$ alkyl wherein the aryl is phenyl, and wherein the aryl is optionally mono or di-substituted, the substituents being each independently $C_{1-6}$alkyl, halo, hydroxy or $C_{1-6}$alkoxy;
AA2 is an amino acid of formula AII

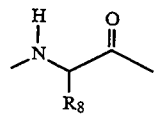

AA3 is an amino acid of formula AIII

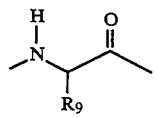

$R_8$ is $C_{1-6}$alkyl; and
$R_9$ is
  (a) hydrogen,
  (b) $C_{1-6}$alkyl,
  (c) amino $C_{1-4}$alkyl,
  (d) N-carbobenzoxy-amino-(n-butyl),
  (e) substituted phenyl $C_{1-6}$alkyl, wherein the substituent is hydrogen, hydroxy, or $C_{1-4}$alkyl.

2. A compound of formula I according to claim 1

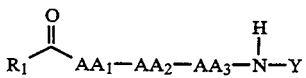

or a pharmaceutically acceptable salt thereof: wherein Y is:

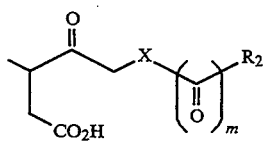

X is O;
m is 0; and
$R_1$ is $C_{1-3}$alkyl or substituted aryl $C_{1-6}$ alkyl wherein aryl is phenyl and the substituent is hydrogen, hydroxy, halo or $C_{1-4}$ alkyl;
$R_2$ is
  (a) tetra or penta substituted phenyl wherein the substitutents are individually selected from the group consisting of
    (1) halo,
    (2) hydroxy, and
    (3) methyl,
  (b) di or tri substituted phenyl, wherein the substituents are individually selected from the group consisting of
    (1) halo,
    (2) methyl,
    (3) trifluoro methyl, and AA1 is a single bond or an amino acid of formula AI

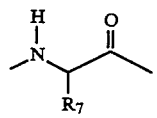

wherein $R_7$ is selected from the group consisting of aryl $C_{1-6}$ alkyl wherein the aryl is phenyl, and wherein the aryl is optionally mono or di-substituted, the substituents being each independently $C_{1-4}$alkyl, halo or hydroxy;

$AA_2$ is an amino acid of formula AII

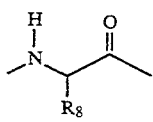

$AA_3$ is an amino acid of formula AIII

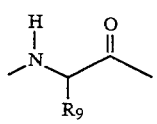

$R_8$ is $C_{1-6}$alkyl; and
$R_9$ is
 (a) hydrogen, or
 (b) substituted phenyl $C_{1-6}$alkyl, wherein the substituent is hydrogen, hydroxy or $C_{1-4}$alkyl.

3. A compound of formula I according to claim 2

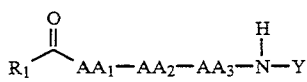

wherein Y is:

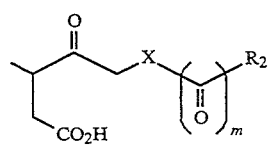

X is O;
m is 0;
$R_1$ is methyl or phenyl $C_{1-6}$ alkyl or hydroxy-phenyl $C_{1-6}$ alkyl;
$R_2$ is pentafluorophenyl;
$AA_1$ is a single bond or tyrosinyl, homotyrosinyl or phenylalaninyl, homophenylalaninyl;
$AA_2$ is

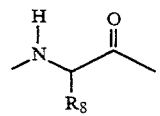

wherein $R_8$ is $C_{1-4}$ alkyl; and
$AA_3$ is alaninyl, lysinyl or ε-CBZ-lysinyl.

4. A compound according to claim 3 wherein $R_1$ is methyl;
$AA_1$ is tyrosinyl, homotyrosinyl, phenylalaninyl, or homophenylalaninyl;
$AA_2$ is

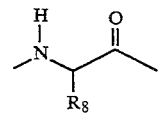

wherein $R_8$ is $C_{1-4}$ alkyl; and
$AA_3$ is alaninyl, lysinyl or ε-CBZ-lysinyl.

5. A compound according to claim 4 wherein
$R_1$ is methyl;
$AA_1$ is tyrosinyl;
$AA_2$ is valinyl, leucinyl or isoleucinyl; and
$AA_3$ is alaninyl, lysinyl or ε-CBZ-lysinyl.

6. A compound according to claim 5 wherein
$R_1$ is methyl;
$AA_1$ is tyrosinyl;
$AA_2$ is valinyl;
$AA_3$ is alaninyl, lysinyl or ε-CBZ-lysinyl.

7. A compound according to claim 3 wherein $R_1$ is methyl or phenyl $C_{1-6}$ alkyl or hydroxy-phenyl $C_{1-6}$ alkyl;
AA1 is a single bond;
AA2 is

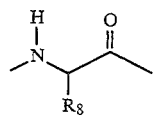

wherein $R_8$ is $C_{1-4}$ alkyl; and
AA3 is alaninyl, lysinyl or ε-CBZ-lysinyl.

8. A compound according to claim 7 wherein $R_1$ is phenyl ethyl or hydroxy-phenyl ethyl.

9. A compound of formula I

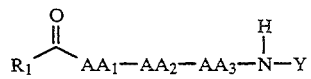

or a pharmaceutically acceptable salt thereof thereof:
wherein Y is:

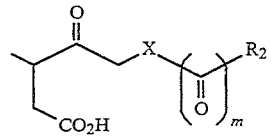

X is O;
m is 1; and
$R_1$ is $C_{1-3}$alkyl or substituted aryl $C_{1-6}$ alkyl wherein aryl is phenyl and the substituent is hydrogen, hydroxy, halo or $C_{1-4}$ alkyl;
$R_2$ is (a) tetra or penta substituted phenyl wherein the substitutents are individually selected from the group consisting of
 (1) methoxy,
 (2) halo,
 (3) hydroxy, and
 (4) $C_{1-3}$alkyl,
(b) di or tri substituted phenyl, wherein the substituents are individually selected from the group consisting of
 (1) halo,
 (2) $C_{1-3}$alkyl,
 (3) trifluoro methyl, and
AA1 is a single bond or an amino acid of formula AI

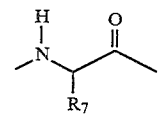

wherein $R_7$ is selected from the group consisting of aryl $C_{1-6}$ alkyl wherein the aryl is phenyl, and wherein the aryl is optionally mono or di-substituted, the substituents being each independently $C_{1-6}$alkyl, halo, hydroxy or $C_{1-6}$alkoxy;

$AA_2$ is an amino acid of formula AII

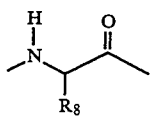

$AA_3$ is an amino acid of formula AIII

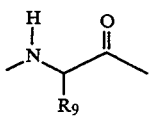

$R_8$ is $C_{1-6}$ alkyl; and
$R_9$ is
 (a) hydrogen,
 (b) $C_{1-6}$alkyl,
 (c) amino $C_{1-4}$ alkyl,
 (d) N-carbobenzoxy-amino-(n-butyl),
 (e) substituted phenyl $C_{1-6}$alkyl, wherein the substituent is hydrogen, hydroxy, carboxy, or $C_{1-4}$alkyl.

10. A compound of formula I according to claim 9

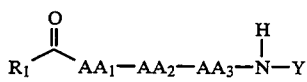

or a pharmaceutically acceptable salt thereof:
 wherein Y is:

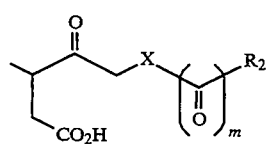

X is O;
m is 1; and
$R_1$ is $C_{1-3}$alkyl or substituted aryl $C_{1-6}$ alkyl wherein aryl is phenyl and the substituent is hydrogen, hydroxy, halo or $C_{1-4}$ alkyl;
$R_2$ is
 (a) tetra or penta substituted phenyl wherein the substitutents are individually selected from the group consisting of
  (1) halo,
  (2) hydroxy, and
  (3) methyl,
 (b) di or tri substituted phenyl, wherein the substituents are individually selected from the group consisting of
  (1) halo,
  (2) methyl,
  (3) trifluoro methyl, and
  (4) $C_{1-3}$alkylcarbonyl;
AA1 is a single bond or an amino acid of formula AI

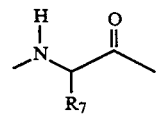

wherein $R_7$ is selected from the group consisting of aryl $C_{1-6}$ alkyl wherein the aryl is phenyl, and wherein the aryl is optionally mono or di-substituted, the substituents being each independently $C_{1-4}$alkyl, halo or hydroxy;

$AA_2$ is an amino acid of formula AII

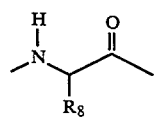

$AA_3$ is an amino acid of formula AIII

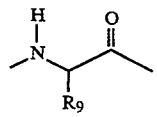

$R_8$ is $C_{1-6}$alkyl; and
$R_9$ is
 (a) hydrogen, or
 (b) substituted phenyl $C_{1-6}$alkyl, wherein the substituent is hydrogen, hydroxy or $C_{1-4}$alkyl.

11. A compound of formula I according to claim 10

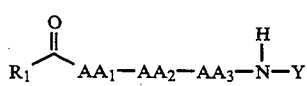

or a pharmaceutically acceptable salt thereof:
 wherein Y is:

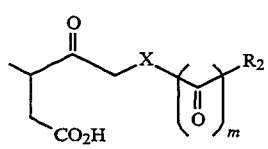

X is O;
m is 1; and
$R_1$ is methyl or phenyl $C_{1-6}$ alkyl or hydroxy-phenyl $C_{1-6}$ alkyl;
$R_2$ is
 (a) pentafluoro phenyl or 2,3,4,6-tetramethyl-4-carboxy phenyl, or 2,6-dichlorophenyl, or
 (b) 2,6-dimethyl-4-cyano phenyl or 2,6-dimethyl-4-trimethylamino phenyl, or
 (c) 2,4,6-trimethyl or 2,6-dimethylphenyl or 2,6-bistrifluoromethyl or 2,4,6-tris-trifluoromethyl;
AA1 is a single bond or tyrosinyl, homotyrosinyl, phenylalaninyl or homophenylalaninyl;
$AA_2$ is an amino acid of formula AII

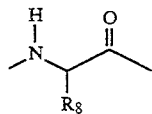

wherein $R_8$ is $C_{1-4}$ alkyl; and
AA$_3$ is alaninyl, lysinyl or ε-CBZ-lysinyl.

12. A compound according to claim 11 wherein
$R_1$ is methyl;
AA$_1$ is tyrosinyl, homotyrosinyl, phenylalaninyl or homophenylalaninyl;
AA$_2$ is an amino acid of formula AII

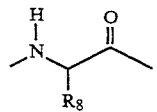

wherein $R_8$ is $C_{1-4}$ alkyl; and
AA$_3$ is alaninyl, lysinyl or ε-CBZ-lysinyl.

13. A compound according to claim 12 wherein
$R_1$ is methyl;
AA$_1$ is tyrosinyl;
AA$_2$ is valinyl, leucinyl or isoleucinyl; and
AA$_3$ is alaninyl, lysinyl or ε-CBZ-lysinyl.

14. A compound according to claim 13 wherein
$R_1$ is methyl;
AA$_1$ is tyrosinyl;
AA$_2$ is valinyl;
AA$_3$ is alaninyl, lysinyl or ε-CBZ-lysinyl.

15. A compound according to claim 11 wherein
$R_1$ is methyl or phenyl $C_{1-6}$ alkyl or hydroxy-phenyl $C_{1-6}$ alkyl;
AA1 is a single bond;
AA2 is wherein $R_8$ is $C_{1-4}$ alkyl; and
AA3 is alaninyl, lysinyl or ε-CBZ-lysinyl.

16. A compound according to claim 15 wherein $R_1$ is phenyl ethyl or hydroxy-phenyl ethyl.

17. A compound selected from the group consisting of:
(a) N-(N-phenylpropionyl-valinyl-alaninyl)-3-amino-4-oxo-5-(2,6-bistrifluoromethylbenzoyloxy) pentanoic acid;
(b) N-(N-phenylpropionyl-valinyl-alaninyl)-3-amino-4-oxo-5-benzoyloxy pentanoic acid; and
(c) N-(N-Acetyl-tyrosinyl-valinyl-alaninyl)-3-amino-4-oxo-5-(pentafluorobenzoyloxy) pentanoic acid.

* * * * *